(12) United States Patent
Indermuhle

(10) Patent No.: US 8,697,005 B2
(45) Date of Patent: Apr. 15, 2014

(54) ASSEMBLIES FOR MULTIPLEX ASSAYS

(76) Inventor: Pierre F. Indermuhle, Berkeley, CA (US)

( * ) Notice: Subject to any disclaimer, the term of this patent is extended or adjusted under 35 U.S.C. 154(b) by 416 days.

(21) Appl. No.: 13/195,922

(22) Filed: Aug. 2, 2011

(65) Prior Publication Data

US 2012/0028847 A1 Feb. 2, 2012

Related U.S. Application Data

(60) Provisional application No. 61/370,080, filed on Aug. 2, 2010.

(51) Int. Cl.
*G01N 21/75* (2006.01)
*B01L 3/00* (2006.01)

(52) U.S. Cl.
CPC .......... *B01L 3/50857* (2013.01); *Y10S 436/809* (2013.01); *Y10S 435/809* (2013.01)
USPC ............. 422/401; 422/65; 422/400; 422/407; 422/412; 422/500; 422/551; 422/553; 422/560; 422/561; 422/942; 422/946; 422/947; 422/948; 436/809; 436/157; 435/3; 435/285.1; 435/286.1; 435/286.2; 435/287.2; 435/288.1; 435/288.4; 435/288.7; 435/303.1; 435/34; 435/374; 435/809; 435/6.14; 435/7.1; 435/91.2

(58) Field of Classification Search
CPC .................................................. B01L 3/50857
USPC .......... 422/65, 400, 401, 407, 412, 500, 551, 422/553, 560, 561, 942, 946, 947, 948; 435/3, 285.1, 286.1, 286.2, 287.2, 435/288.1, 288.4, 288.7, 303.1, 34, 374, 6, 435/6.14, 7.1, 91.2, 809; 436/809, 157
See application file for complete search history.

(56) References Cited

U.S. PATENT DOCUMENTS

| | | | | |
|---|---|---|---|---|
| 3,730,352 | A * | 5/1973 | Cohen et al. | 210/332 |
| 4,902,481 | A * | 2/1990 | Clark et al. | 422/535 |
| 5,047,215 | A * | 9/1991 | Manns | 422/534 |
| 5,679,310 | A * | 10/1997 | Manns | 422/553 |
| 6,027,627 | A * | 2/2000 | Li et al. | 204/603 |
| 6,436,632 | B2 * | 8/2002 | Schellenberger et al. | 435/4 |
| 6,485,690 | B1 * | 11/2002 | Pfost et al. | 422/552 |
| 6,924,107 | B2 * | 8/2005 | Liu | 435/6.11 |
| 6,969,489 | B2 * | 11/2005 | Freeman | 422/504 |

(Continued)

*Primary Examiner* — Dennis M White

(57) ABSTRACT

Multiplex binding assay assemblies are disclosed. The assemblies include at least one assay bar that has a top side, a bottom side, and at least one well accessible from the top side of the assay bar, with each well including a side surface, a bottom surface, an open top end. Each well also includes at least one secondary container, with each secondary container including a capillary tube that (i) begins at a location within an interior volume of the well and (ii) ends at a location beneath the bottom side of the assay bar. The assemblies further include a guiding track, which includes a set of two rails, with each rail having its own separate groove. Such grooves are configured to run parallel to each other with a distance between such grooves, with a first groove configured to receive a protruding element (or an end) of a first side of the assay bar, and a second groove configured to receive a protruding element (or an end) of a second side of the assay bar. The set of two separate grooves are configured to allow the assay bar to glide along the grooves from one side to a second side of the guiding track.

20 Claims, 14 Drawing Sheets

(56) References Cited

U.S. PATENT DOCUMENTS

| | | | |
|---|---|---|---|
| 7,156,996 B2* | 1/2007 | Watzele et al. | 210/321.71 |
| 7,280,727 B1* | 10/2007 | Barbedette et al. | 385/120 |
| 7,666,360 B2* | 2/2010 | Schellenberger et al. | 422/552 |
| 8,105,554 B2* | 1/2012 | Kanigan et al. | 422/504 |
| 2001/0002984 A1* | 6/2001 | Vetter | 422/102 |
| 2002/0164824 A1* | 11/2002 | Xiao et al. | 436/524 |
| 2003/0003036 A1* | 1/2003 | Rouleau et al. | 422/245.1 |
| 2003/0049862 A1* | 3/2003 | He et al. | 436/180 |
| 2003/0087454 A1* | 5/2003 | Schultz et al. | 436/161 |
| 2003/0148504 A1* | 8/2003 | Duong et al. | 435/287.2 |
| 2005/0271553 A1* | 12/2005 | Ramstad et al. | 422/101 |
| 2006/0051250 A1* | 3/2006 | Gonzalez et al. | 422/102 |
| 2007/0031282 A1* | 2/2007 | Zucchelli et al. | 422/57 |
| 2009/0258797 A1* | 10/2009 | Hunter et al. | 506/40 |
| 2011/0312531 A1* | 12/2011 | Jacobs et al. | 506/9 |

* cited by examiner

ASSEMBLIES FOR MULTIPLEX ASSAYS

CROSS-REFERENCE TO RELATED APPLICATIONS

This application claims priority to, and incorporates by reference, U.S. provisional patent application Ser. No. 61/370,080, which was filed on Aug. 2, 2010.

FIELD OF THE INVENTION

The field of the present invention relates to assemblies for use in multiplex binding assays. More particularly, the field of the present invention relates to reagent dispensers, stackable assay bars, and guiding tracks for assembling such assay bars, which may be used to carryout multiplex binding assays.

BACKGROUND OF THE INVENTION

The 96-well microplate and related versions thereof, such as 384-well microplates, continue to play a critical role in the field of analytical assays. Indeed, such microplates are ubiquitously employed in research laboratories, analytical laboratories, and medical diagnostic laboratories throughout the world. For many years, there has been a growing demand for methods that enable investigators and laboratories to perform multiplex assays using these standard microplate formats.

A multiplex assay is a type of procedure that simultaneously—in a single assay—measures, detects and/or analyzes multiple analytes. Multiplex assays have been used in order to detect or quantify various biomolecules in a particular sample, such as mRNAs, proteins, antibodies, and other biomolecules. Multiplex assay formats are often beneficial, insofar as such formats can provide a significant reduction in assay costs, on a cost-per-analyte basis. In addition, such formats significantly increase the amount (and often types) of information that can be extracted from each sample, particularly on a per-sample-volume basis.

Despite the significant utility of multiplex assay formats, present platforms do not allow for the dispensing of a specific secondary binding agent (i.e., the detection agent) to each of a plurality of immobilized targets, in order to reduce cross-reactivity (which leads to false positive results). This drastically limits the types of assays that may be combined in a multiplex fashion (and, more particularly, the combination of analytes that may be measured or detected in a single assay format). In addition, current platforms do not allow individual assay conditions, e.g., sample dilutions, buffer types, incubation times, etc., to be optimized. Accordingly, a continuing need exists for new and improved multiplex binding assay assemblies and methods of use thereof.

SUMMARY OF THE INVENTION

According to certain aspects of the present invention, multiplex binding assay assemblies are provided. The assemblies generally include at least one assay bar that has a top side, a bottom side, and at least one well accessible from the top side of the assay bar, with each well including a side surface, a bottom surface, and an open top end. The invention provides that each well also includes at least one secondary container, with each secondary container including a capillary tube that (i) begins at a location within the interior volume of the well and (ii) ends at a location beneath the bottom side of the assay bar.

According to such aspects of the invention, such assemblies further include a dispenser bar that is adapted to be positioned adjacent to the top side of a first assay bar included within a plurality of assay bars, when the assay bars are stacked upon each other. According to such embodiments, the first assay bar is positioned at the top of the stack, such that the dispenser bar may be stacked on top of the first assay bar. As explained herein, the dispenser bar will comprise multiple reservoirs, each of which are configured to provide one or more reagents to a single secondary container located in a well of the first assay bar.

As described further below, each secondary container comprises a capillary tube that exhibits a length that is approximately equal to a distance between the top side and the bottom side of the assay bar. In certain embodiments, the top end of each secondary container may be recessed (within the wells) relative to the top side of the assay bar, with a bottom end of each secondary container extending below a plane that runs tangential with the bottom side of the assay bar. The invention provides that the arrangement of the plurality of secondary containers is preferably identical among all of the wells contained in all of the plurality of assay bars. Still further, the invention provides that upon stacking the plurality of assay bars upon each other, the secondary containers of the first assay bar are in fluid communication with the secondary containers of a second assay bar stacked directly beneath the first assay bar (and all other assay bars stacked directly beneath the second assay bar). According to such embodiments, the invention provides that a bottom end and top end of each secondary container of the assay bars are open, such that liquid may travel from each secondary container of a first assay bar to an adjacent secondary container of a second assay bar. The invention provides that the liquid will be retained within the secondary containers of the assay bars due to capillary forces.

The multiplex binding assay assemblies of the present invention further encompass a guiding track, which is configured to hold and orient the assay bars described herein. The guiding track may also be used to re-orient the assay bars from a stacked position to a side-by-side position. According to certain embodiments, the guiding tracks of the present invention generally comprise a set of two rails running parallel to each other, with a first rail being configured to receive a first end of an assay bar, and a second rail being configured to receive a second end of the same assay bar, such that the assay bar is held perpendicularly to each rail. The guiding track is preferably configured to allow the assay bar to move (slide) linearly along the set of two rails, and to rotate about a longitudinal axis of the assay bar (which facilitates the re-orientation of the assay bar from a stacked position to a side-by-side position).

The invention provides that the guiding track may exhibit various forms. For example, as described further below, the guiding tracks may comprise an L-shaped guiding track, which includes a vertical portion (that is configured to hold a plurality of assay bars in a stacked orientation) and a horizontal portion (that is configured to hold a plurality of assay bars in a side-by-side orientation). In other examples, the guiding tracks may exist within a single plane, and comprise a groove in each rail, which is configured to receive a protruding element at the end of an assay bar. According to such embodiments, the assay bars may be linearly moved from one side of the groove to the other, whereby such movement causes the assay bars to rotate by approximately 90-degrees, e.g., to cause the assay bars to be re-oriented from a stacked orientation to a side-by-side orientation.

According to yet further aspects of the invention, the guiding tracks may exhibit a frame-like configuration. More particularly, according to this embodiment, the two rails of the guiding track will include two telescoping parts. The telescoping parts are configured to be reversibly (i) extended by pulling such parts away from each other and (ii) contracted by pushing such parts closer to each other. According to these embodiments, the rails of the guiding track will include a set of pads and sliders, which comprise a set of pins and grooves, which together allow a plurality of assay bars connected to the guiding track to rotate around a longitudinal axis of such assay bars by 90-degrees in a first direction, when the telescoping components of such rails are pulled away from each other for a first time. Similarly, the set of pins and grooves, or another set of pins and grooves, allow the assay bars to rotate by 90-degrees around such longitudinal axis in an opposite (second) direction when the telescoping components of such rails are pulled away from each other for a second time. This allows a user of the guiding track to easily and quickly convert the orientation of a set of assay bars from a stacked orientation to a side-by-side orientation (or vice versa).

According to additional aspects of the present invention, methods of using the multiplex binding assay assemblies for carrying out multiplex binding assays are encompassed by the present invention.

The above-mentioned and additional features of the present invention are further illustrated in the Detailed Description contained herein.

DETAILED DESCRIPTION OF THE INVENTION

The following will describe, in detail, several preferred embodiments of the present invention. These embodiments are provided by way of explanation only, and thus, should not unduly restrict the scope of the invention. In fact, those of ordinary skill in the art will appreciate upon reading the present specification and viewing the present drawings that the invention teaches many variations and modifications, and that numerous variations of the invention may be employed, used and made without departing from the scope and spirit of the invention.

Multiplex Assay Assemblies

Referring now to FIGS. 1-6, the invention provides assay bars that may be used to carryout multiplex assays, along with certain guide tracks that may be used or orient such assay bars during the use thereof. As described further below, the assay bars comprise a series of wells 14, with each well including one or more secondary containers 20 disposed therein. The assay bars preferably exhibit a number of wells, and shape and dimension, as that of a row or column from a standard microtiter plate (a.k.a. microplates). For example, an assay bar will preferably consist of 8 or 12 wells (i.e., the number of wells of a column or row of a 96-well microplate)—or 16 or 24 wells (i.e., the number of wells of a column or row of a 384-well microplate). The one or more secondary containers 20 disposed in each well 14 preferably consist of a capillary tube 22, which spans an approximate thickness of the assay bar. As explained further below, the capillary tubes of each well are preferably configured to be in fluidic communication with the secondary containers 20 of other assay bars, when the assay bars are stacked upon each other. This way, reagents and other liquids may be simultaneously loaded into the secondary containers 20, when the assay bars are stacked upon each other (and the secondary containers 20 of the assay bars are in fluidic communication with each other).

Figure 1:
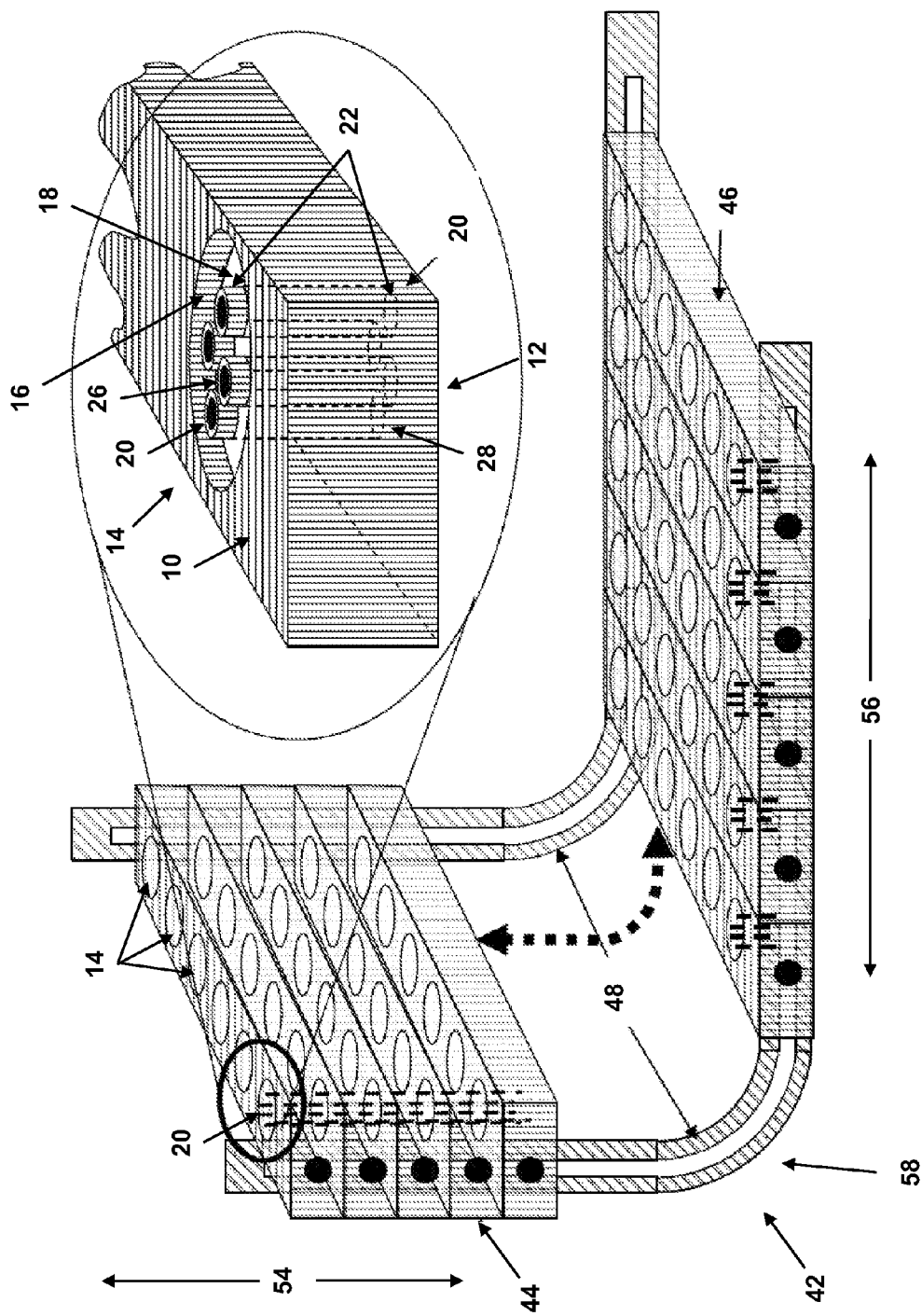
FIG. 1: is a diagram of a guiding track described herein, which has a plurality of assay bars positioned thereon.
Figure 4:
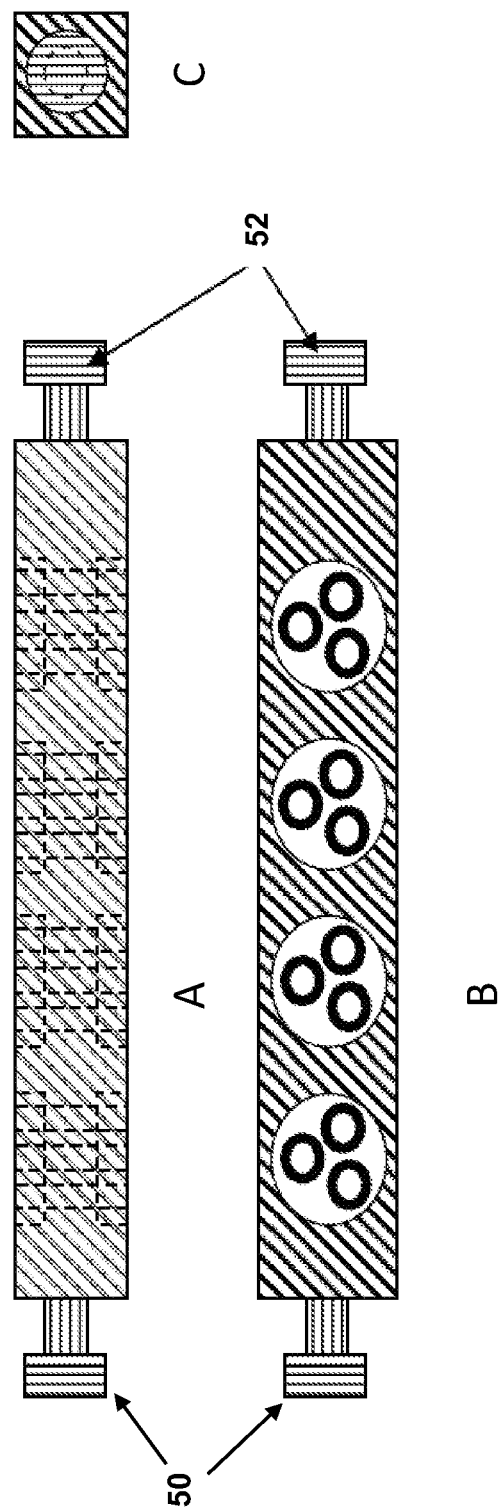
FIG. 4A: is a side transparent view of an assay bar of the present invention.
FIG. 4B: is a top side view of the assay bar of FIG. 4A.
FIG. 4C: is a side view of the assay bar of FIG. 4A.

The multiplex assay assemblies further comprise a guiding track, which may be used to orient the assay bars from a stacked position 44 to a side-by-side position 46, as illustrated in FIG. 1. More particularly, as described further below, the multiplex assay assemblies of the present invention include a guide track, which facilitates the re-orientation of a set of assay bars from a stacked position 44 to a side-by-side position 46 (and vice versa). As described further below, in one embodiment, the guiding track 42 preferably includes a set of grooves 48 (located in separate rails), with a first groove receiving a protruding element 50 of a first end of the assay bars, and a second groove receiving a protruding element 52 of a second end of the assay bars (FIG. 4). In one embodiment, the guiding track 42 is further configured to have at least two planes, with each plane running approximately perpendicular with the other, e.g., a first plane 54 that runs vertically (to orient assay bars in a stacked position 44) and a second plane 56 that runs horizontally (to orient assay bars in a side-by-side configuration 46). As such, a set of assay bars may be engaged within the guiding track and oriented in a stacked position 44 (along the vertically-oriented groove)—and, if desired, converted to a side-by-side orientation 46 by moving the assay bars along the groove 48 of the guiding track 42 to the horizontally-oriented groove. The assay bars, and the guiding tracks, of the present invention are further described below.

Assay Bars

The invention provides that the assay bars generally include a top side 10, a bottom side 12, and at least one secondary container 20 accessible from the top side 10 of the assay bars. In certain embodiments, the assay bars further include at least one well 14 accessible from the top side 10 of the assay bars. According to such embodiments, each well 14 includes a side surface 16 and a bottom surface 18, with the at least one secondary container 20 protruding through the bottom surface 18 of each well 14 (and being accessible from the top side 10 of the assay bar). In certain preferred embodiments, a plurality of secondary containers 20 will protrude through the bottom surface 18 of each well 14 (and be accessible from the top side 10 of the assay bar).

Figure 2:
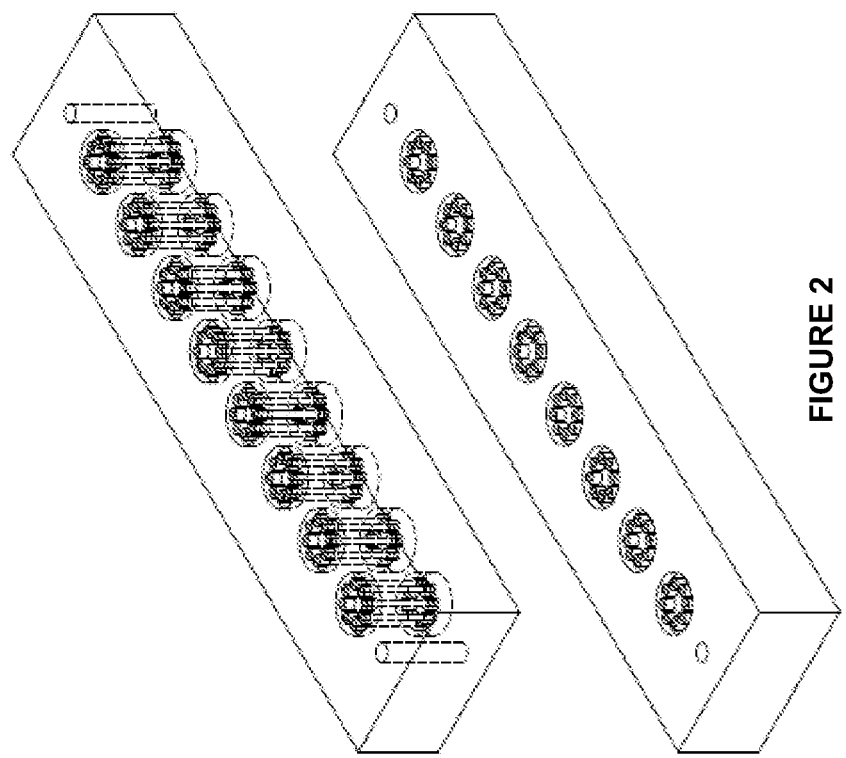
FIG. 2: is a diagram of a non-limiting example of the assay bars described herein, which comprise eight separate wells, with each well including a grouping of eight secondary containers.
Figure 3:
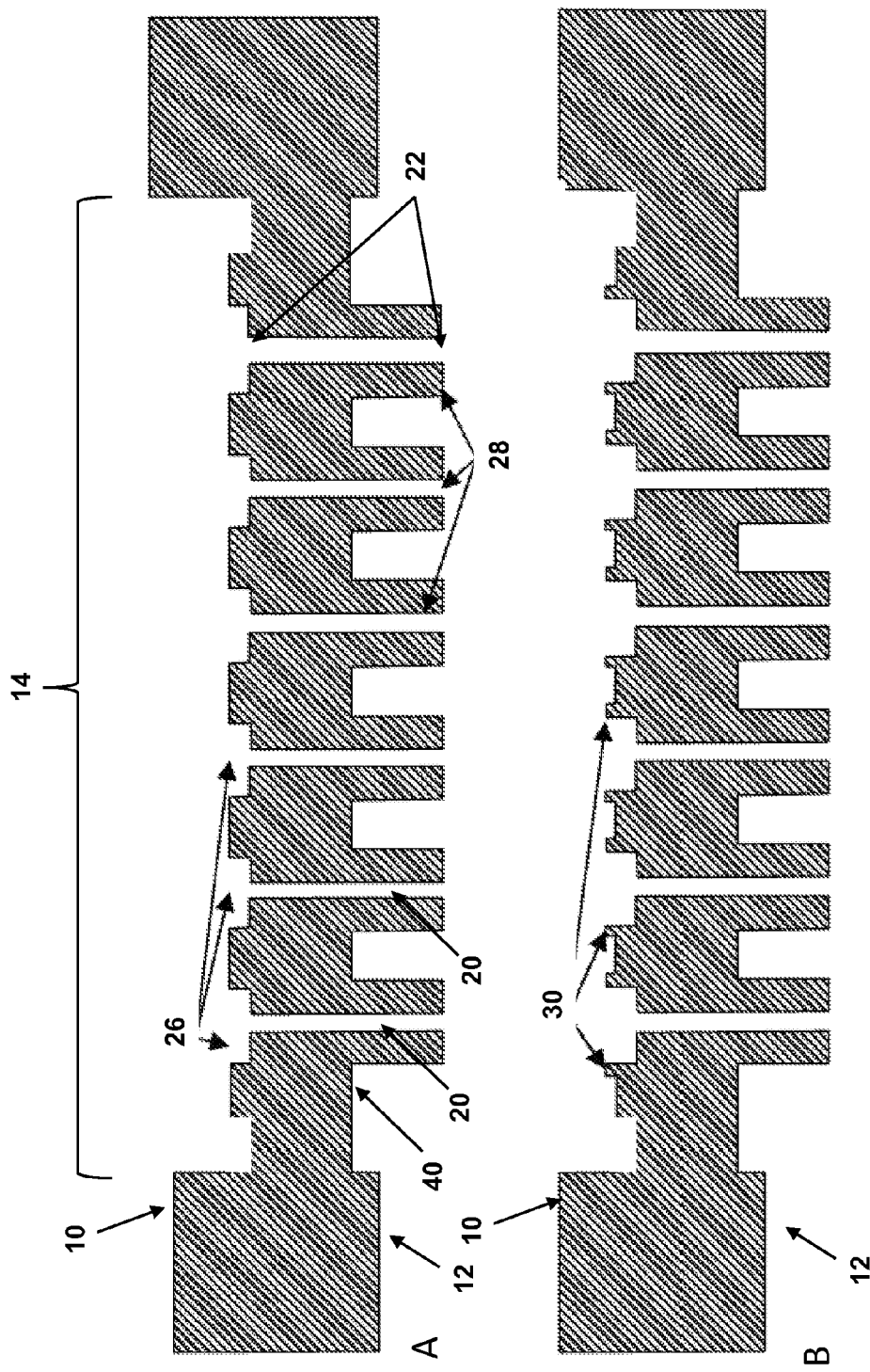
FIG. 3A: is a cross-sectional diagram of an assay bar of the present invention in which the top ends of the secondary containers are recessed relative to the top surface of the assay bar (with the secondary containers protruding through the bottom surface of the surrounding well).
FIG. 3B: is a cross-sectional diagram of an assay bar of the present invention in which the top ends of the secondary containers are recessed relative to the top surface of the assay bar, and each secondary container further includes a protruding edge (at the top end thereof).

According to certain preferred embodiments, the secondary containers 20 consist of a capillary tube 22, which may span a distance (length) that is equal to the thickness (or approximately equal to the thickness) of the assay bar, with the "thickness" of the assay bar being the distance between the top side 10 and bottom side 12 thereof. The invention provides that the location and arrangement of the secondary containers 20 in each well 14 will preferably be identical among the assay bars, such that the secondary containers 20 of multiple assay bars are aligned and directly adjacent to each other when the assay bars are stacked upon each other, as illustrated in FIGS. 1 and 2.

That is, when the assay bars are stacked upon each other in an aligned manner, the bottom end 28 of each secondary container 20 of a first assay bar is aligned with and adjacent to the top end 26 of a corresponding secondary container 20 of the underlying assay bar. This provides for fluid communication between the secondary containers 20 of stacked assay bars, such that a dispenser bar 24 (described below) may be used to deliver reagents to the secondary containers 20 of multiple assay bars at the same time (when such assay bars are stacked upon each other).

According to certain embodiments of the invention, the secondary containers 20 may begin at a top end 26 that is located at (or near) a plane that runs tangential to the top side 10 of the assay bar. According to such embodiments, the bottom ends 28 of the secondary containers 20 will preferably be located at (or near) a plane that runs tangential with the bottom side 12 of the assay bar. As such, the top ends 26 and bottom ends 28 of the secondary containers 20 will span the entire width or thickness of the assay bar. As explained above, this configuration allows the secondary containers 20 of a first assay bar to be located directly adjacent to, and in fluid communication with, the secondary containers 20 of a second assay bar, when such assay bars are stacked upon each other. The invention provides that the bottom side 12 of the assay bar may, optionally, comprise a recess 40 around each secondary container 20.

According to certain additional embodiments of the invention, the secondary containers 20 may begin at a top end 26 that protrudes through the bottom surface 18 of a well 14, and into an interior volume thereof, but ends prior to reaching a plane that runs tangential to the top side 10 of the assay bar. That is, the top ends 26 of the secondary containers 20 may be recessed relative to the top side 10 of the assay bar. According to such embodiments, the bottom ends 28 of the same secondary containers 20 may extend beyond a plane that runs tangential with the bottom side 12 of the assay bar. Preferably, according to such embodiments, the bottom ends 28 of the secondary containers 20 will extend beyond such bottom side 12 by a distance $\Delta_1$, wherein the distance of $\Delta_1$ represents the distance between the top end 26 of each secondary container 20 and the top side 10 of the assay bar.

This way, as explained above, multiple assay bars may be stacked upon each other, with the secondary containers 20 of the stacked assay bars being directly adjacent to and in fluid communication with each other. That is, when the bottom ends 28 of the secondary containers 20 extend beyond the bottom side 12 of the assay bar by a distance $\Delta_1$, such bottom ends 28 will be of sufficient length to be located directly adjacent to the recessed top ends 26 of the secondary containers 20 in the assay bar located (stacked) directly beneath it. As explained above, this provides for fluid communication between the secondary containers 20 of stacked assay bars, such that a dispenser bar 24 may be used to simultaneously deliver reagents to the secondary containers 20 of multiple assay bars (when such assay bars are stacked upon each other).

The well 14 may be used as a reservoir to deliver a reagent (or sample) to the one or more secondary containers 20 located within such well 14. More particularly, when the top ends 26 of the secondary containers 20 are recessed relative to the top side 10 of the assay bar, a reagent (or sample) may be dispensed into the well 14. If such reagent (or sample) is dispensed into the well 14 to a volume that causes such reagent to exceed the extent to which the secondary containers 20 protrude into the interior of such well 14, the reagent (or sample) will flow into the secondary containers 20 located therein. As such, the well 14 may also be used as a reservoir to deliver a reagent (or sample) to the one or more secondary containers 20 located within such well 14.

Referring to FIG. 3B, the invention provides that the recessed top ends 26 of the secondary containers 20 may comprise a protruding edge 30, which is effective to facilitate control and retention of reagent (or sample) inside the secondary containers 20. Additionally, the invention provides that such protruding edge 30 may comprise one or more notches (located on the top surface of the protruding edges 30), which will facilitate the transfer of liquid into the interior of the secondary containers 20. Still further, the invention provides that the top ends 26 and/or bottom ends 28 of the secondary containers 20 may be configured to improve and facilitate the transfer of reagent from one secondary container 20 (of a first assay bar) to another secondary container 20 (of a second assay bar). For example, the ends of the secondary containers 20 may be beveled, indented, or exhibit other configurations that would facilitate the transfer of reagent from one secondary container 20 to another.

The invention provides that when the secondary containers 20 are cylindrical, the secondary containers 20 will exhibit a diameter of about 1 millimeter (or less) or, alternatively, may exhibit a diameter of 500 micrometers, 200 micrometers, or 100 micrometers (or other diameters within such ranges). When the secondary containers 20 are configured in such manner, surface tension forces dominate liquid behavior, and will cause reagents loaded into the secondary containers 20 to be pulled into and contained within the secondary containers 20. A capillary barrier will retain the reagent within the secondary containers 20, until otherwise drawn therefrom by force (e.g., during a reagent decanting step) or by making contact with another secondary container 20 of another assay bar, e.g., when multiple assay bars are stacked upon each other.

The invention provides that reagent will not leak from the secondary containers 20 as a result of these capillary forces (capillary barriers). As such, once the secondary containers 20 of multiple stacked assay bars have been filled with reagent, the assay bars may be separated from each other for further processing (e.g., and oriented in a side-by-side manner as described below), and the reagent will remain in such secondary containers 20 vis-à-vis capillary forces (capillary barriers). If the reagent contains magnetic micro-beads, magnets may be used to prevent the beads from falling out of the secondary containers 20, e.g., during decanting and rinsing steps. That is, the assay bars may comprise a magnetic bar that may be reversibly affixed to the assay bar, which is positioned in sufficient proximity to the secondary containers 20 to magnetically retain any magnetic micro-beads that may be contained within a reagent, inside the secondary containers 20.

According to certain preferred embodiments of the present invention, the assay bars of the present invention may comprise a plurality of wells 14—each of which may have one or more secondary containers 20 and, preferably, will comprise multiple secondary containers 20. For example, the assay bars of the present invention may exhibit a length (or width) that is equal to, or approximately equal to, the length of a standard 96-well plate. According to such example, the assay bar may comprise 8, 12, 16, or 24 groups of secondary containers 20, with each group of secondary containers 20 optionally being contained within its own well 14, as illustrated, for example, in FIG. 2. According to such embodiments, each group of secondary containers 20 may comprise from 2-20 secondary containers 20. The thickness of the assay bars may range between, for example, 10-15 millimeters, with the length of the secondary containers 20 preferably being consistent with such thickness, i.e., from 10-15 millimeters. However, in certain alternative embodiments, the length of the secondary containers 20 may be less than the thickness of the assay bar, e.g., the secondary containers 20 may exhibit a length that ranges from 5-10 millimeters.

As described above, the invention provides that the secondary containers 20 included in the wells 14 may be open at both ends, i.e., at the opening within the well 14 (at the top end 26 of each secondary container 20) and at an opening located at (or below) the bottom side 12 of the assay bar (at the bottom end 28 of each secondary container 20). According to yet further embodiments of the present invention, however, the secondary containers 20 may comprise a restriction located at (or near) the bottom ends of the secondary containers 20. The restriction will preferably be effective to retain liquid inside of the secondary containers 20 through capillary forces. This restriction may be integrally formed with the secondary containers 20. Alternatively, the restrictions may be applied, when needed, to the bottom ends 28 of the secondary containers 20 during the performance of an assay.

According to such embodiments, the "restriction" may comprise, by way of example and not limitation, a narrowing of the bottom end 28 of the secondary container 20 (to reduce the size/diameter of the aperture at the bottom end 28 thereof to encourage a capillary barrier). Alternatively, the restriction may comprise a circular disc, which includes an aperture smaller than the aperture (internal diameter) of the secondary container 20, which may be applied to the bottom end 28 of the secondary container 20. Such a disc may be made out of hydrophobic material or be coated with a hydrophobic layer. Still further, the restriction may consist of a grid, with a mesh size smaller than the aperture of the secondary container 20, which may be applied to the bottom end 28 of the secondary container 20. This geometry is advantageous insofar as it only requires a relatively low precision alignment, relative to the end of the secondary container 20. Such a grid may be comprised of hydrophobic material or be coated with a hydrophobic layer.

In addition, the restriction may comprise a porous membrane that may be applied to the bottom end 28 of a secondary container 20. According to yet further non-limiting examples, the restriction may comprise a restriction bar, which includes an array of features that may be applied to the bottom ends 28 of all secondary containers 20 included within an assay bar. The dimensions of this restriction bar will preferably match the dimensions of the assay bar, with the secondary containers 20 positioned such that both bars may be aligned respective to each other—with the flow restrictive features being applied to the bottom ends 28 of all secondary containers 20. The restrictive features may protrude from the surface of the restriction bar, so that they may be easily positioned in a manner that is adjacent to the bottom ends 28 of the secondary containers 20.

Dispenser Bars

Figure 6:
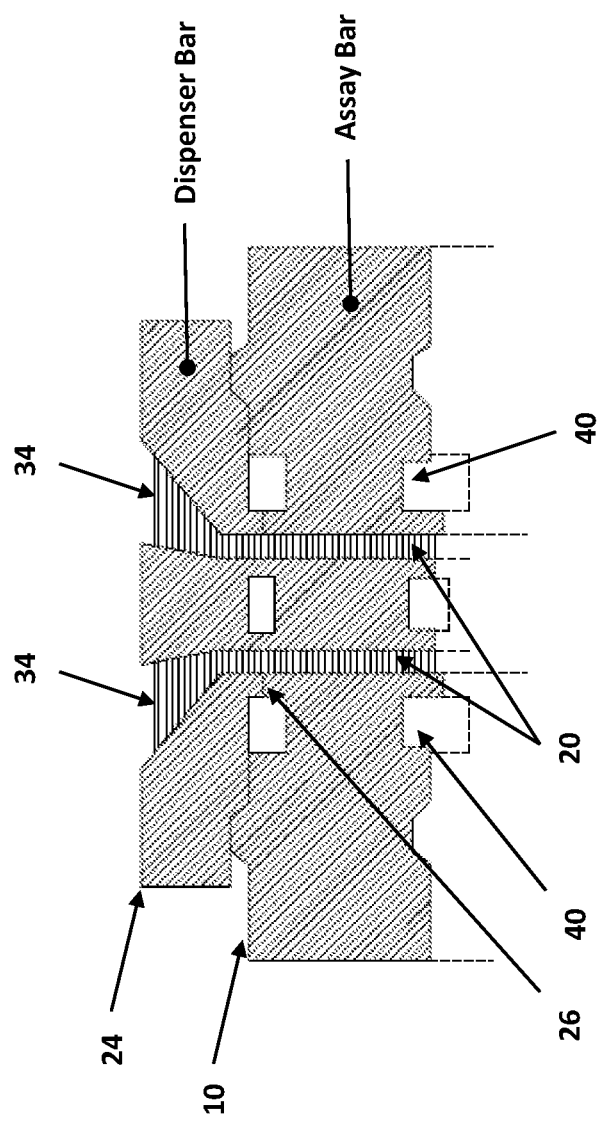
FIG. 6 is a side, cross-sectional view of a dispenser bar positioned on the top of an assay bar, as described herein.

Referring to FIG. 6, the present invention further encompasses a dispenser bar 24, which is configured and adapted to be positioned adjacent to the top side 10 of the assay bars. The dispenser bar 24 is configured to provide one or more reagents to the one or more secondary containers 20 of an assay bar. More particularly, the dispenser bar 24 is configured and adapted to be positioned (and mounted) adjacent to the top side 10 of the assay bars, such that it may directly provide one or more reagents to the one or more secondary containers 20 of an assay bar.

Still referring to FIG. 6, the invention provides that the dispenser bar 24 comprises at least one reservoir 34 (and preferably multiple reservoirs 34), which is in fluid communication with the top end 26 of the secondary container 20 (e.g., the portion that protrudes through the bottom surface 18 of the well 14 and into an interior volume thereof), when the dispenser bar 24 is positioned adjacent to the top side 10 of the assay bar. Preferably, the reservoir(s) 34 will exhibit a larger diameter (or cross-section when viewed from above), relative to the diameter (or cross-section) of the secondary containers 20, such that reagents may be easily and manually added to such reservoir(s) 34—e.g., using a micropipette, robotics, or other similar devices. In such embodiments, the reservoir(s) 34 may exhibit a type of funnel configuration, with the diameter narrowing as it reaches an adjacent secondary container 20 of an underlying assay bar.

The invention provides that the same reagent may be provided to each reservoir 34 of the dispenser bar 24 or, alternatively, different reagents may be provided to such reservoirs 34. This way, if desirable, the same well 14 may be provided with multiple types of reagents, with different reagents being provided to the different secondary containers 20 of a particular well 14 via the separate reservoirs 34 of the dispenser bar 24.

The invention provides that the reservoirs 34 of a dispenser bar 24 may be filled with a reagent, such that the dispenser bar 24 may then be aligned with and placed over an assay bar (or set of stacked assay bars), in order to then fill the secondary containers 20 of such assay bars as described herein. Alternatively, the dispenser bar 24 may first be aligned with and placed over an assay bar (or set of stacked assay bars), and then filled with a reagent, which will then travel from the dispenser bar 24 and into the secondary containers 20 of the assay bars. The invention provides that the dispenser bar 24 may comprise aligning elements, which may be used to properly align and position the dispenser bar 24 on top of an assay bar.

The invention provides that desired reagents or other liquids will travel from the reservoirs 34 of the dispenser 24 and into the secondary containers 20 of an assay bar by way of capillary forces. The invention provides that the protruding edges 30 (FIG. 3) at the top ends 26 of the secondary containers 20 may be inserted into the separate reservoirs 34 of the dispenser bar 24. For example, upon inserting the protruding edges 30 of a secondary container 20 into a separate reservoir 34 of the dispenser bar 24 that is filled with a reagent, the reagent will travel from the reservoir 34 (and be pulled) into the secondary container 20 by capillary action (and into the secondary containers 20 of assay bars on which a first assay bar is stacked, since the secondary containers 20 of a series of stacked assay bars will be in fluidic communication with each other).

Alternatively, as illustrated in FIG. 6, the invention provides that placing the secondary containers 20 of an assay bar directly adjacent to the reservoirs 34 of the dispenser bar 24 will also cause reagents, samples, or other liquids to travel from the dispenser bar 24 and into the secondary containers 20 by capillary action (without necessarily inserting any protruding edges 30 of the secondary containers 20 into the separate reservoirs 34 as described above). The reagents, samples, or other liquids will stop flowing when the dispenser bar 24 is removed from the assay bar(s), or when the secondary containers 20 become full, due to the capillary barrier that will form at the bottom ends 28 of the secondary containers 20.

The invention provides that the volume of reagent (or other liquid) that the secondary containers 20 of an assay bar will hold may be determined based on the internal volume of the secondary containers 20. For example, in the case of cylindrically-configured secondary containers 20, the volume of such containers may be calculated using the following formula:

$$\text{Volume} = \pi \times r^2 \times h \text{ (pi} \times \text{radius-squared} \times \text{height)}$$

Although the secondary containers 20 are illustrated to be cylindrical (and to therefore have a circular cross-section) in FIGS. 1-6, the invention provides that the secondary containers 20 may exhibit other geometries.

According to certain additional and alternative embodiments of the invention, the secondary containers 20 of the assay bars may be provided with reagent through forces other than capillary action. For example, reagent may be dispensed into the secondary containers 20 through mere gravitational forces or, alternatively, a reagent (or other liquid) may be dispensed therein using an external pressure source (from a pressurized dispenser or other source of reagent, such as single or multiple pipettes).

The invention provides that the assay bars may include an alignment feature (e.g., on the top side 10 of the assay bars), which is configured be positioned adjacent to a correspondingly configured aligning element of a dispenser bar 24, such that when the alignment feature of the assay bar and the correspondingly configured aligning element (on the bottom side) of the dispenser bar 24 are fittingly positioned next to each other, the dispenser bar 24 is properly aligned and positioned adjacent to the top side 10 of the assay bar. For example, the alignment feature (e.g., on the top side 10 of the assay bars) may comprise a protruding element, which is received by an aperture (aligning element) of a dispenser bar 24.

Guiding Tracks

As explained above, the present invention encompasses a guiding track, which is configured to hold and orient the assay bars described herein. The guiding track may also be used to re-orient the assay bars from a stacked position to a side-by-side position. The guiding tracks of the present invention generally comprise a set of two rails running parallel to each other, with a first rail being configured to receive a first end of an assay bar, and a second rail being configured to receive a second end of the same assay bar, such that the assay bar is held perpendicularly to each rail. As described further below, the guiding track is further configured to allow the assay bar to move (slide) linearly along the set of two rails, and to rotate about a longitudinal axis of the assay bar (which facilitates the re-orientation of the assay bar from a stacked position to a side-by-side position). The following will describe several non-limiting examples of the guiding tracks that are encompassed by the present invention.

L-Shaped Guiding Tracks

Referring now to FIG. 1, as explained above, the present invention encompasses a guiding track 42, which is configured to hold and orient the assay bars described herein, and to re-orient the assay bars from a stacked position 44 to a side-by-side position 46. The invention provides that the guiding track 42 preferably includes a set of two grooves 48 (with each groove located in its own rail), running parallel to each other, with a first groove receiving a protruding element 50 of a first end of the assay bars, and a second groove receiving a protruding element 52 of a second end of the assay bars (FIG. 4). According to certain alternative embodiments, the grooves may be configured to be large enough to receive an entire side of an assay bar—instead of just a protruding element 50/52 thereof.

In one embodiment, the guiding track 42 is further configured to have at least two planes, with each plane running approximately perpendicular with the other, e.g., a first plane 54 that runs vertically (to orient assay bars in a stacked position 44) and a second plane 56 that runs horizontally (to orient assay bars in a side-by-side configuration 46). As such, a set of assay bars may be engaged within the guiding track 42 and oriented in a stacked position 44 (along the vertically-oriented groove 48/54)—and, if desired, converted to a side-by-side orientation 46 by moving the assay bars along the groove 48 of the guiding track 42 to the horizontally-oriented groove 48/56. The invention provides that the protruding elements 50/52 of the assay bars are allowed and configured to slide along the groove 48 of the guiding track 42, such that the assay bars may be converted from a stacked position 44 to a side-by-side position 46 (or vice versa).

The invention provides that the intersection 58 of the two planes 54/56 of the guiding track 42 may be configured as a 90-degree turn, i.e., it may exhibit an "L" shaped transition from one plane to the other. Alternatively, as illustrated in FIG. 1, the intersection 58 of the two planes 54/56 of the guiding track 42 may exhibit a gradual, radial turn. The invention provides that the guiding track 42 may be designed to exhibit any desired length along its vertical plane 54 and horizontal plane 56. Of course, the longer the length of each such plane, the more assay bars that the guiding track 42 may accept. Preferably, however, the length of the vertical plane 54 of the guiding track 42 will be substantially the same as (or identical to) the length of its horizontal plane 56.

Still further, according to certain embodiments, the invention provides that the guiding track 42 comprises a locking mechanism—on the vertical plane 54, horizontal plane 56, or both. Such locking mechanism may be employed to lock a series of assay bars into place, so that they cannot move, either in the stacked position 44 or the side-by-side configuration 46. Locking the assay bars into position will be desirable when a user is carrying out a step of an assay, such as loading a reagent into the wells 14 or secondary containers 20 of a set of assay bars when in the stacked position 44 on the vertical plane 54 of the guiding track 42.

Single-Plane Guiding Tracks

Figure 5:
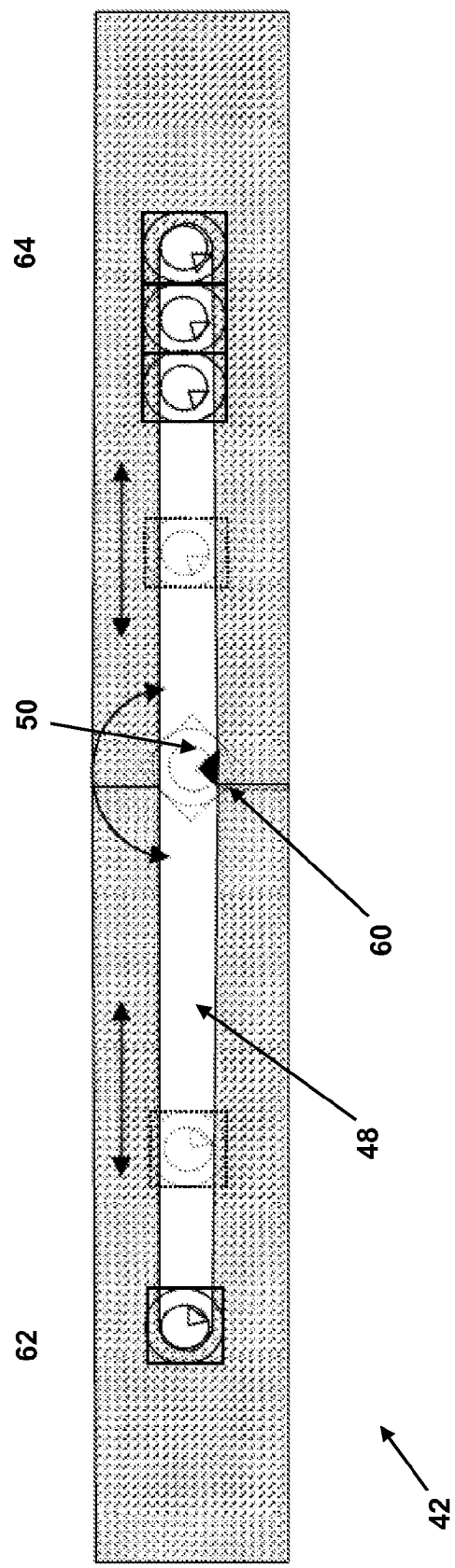
FIG. 5 is a side, cross-sectional view of a guiding track, with several assay bars disposed thereon, which may be converted from one orientation to another in the same plane of the guiding track.

Referring now to FIG. 5, according to certain alternative embodiments of the invention, the guiding track 42 may be straight and exist within a single plane. Preferably, such guiding tracks 42 will include a means for converting assay bars associated therewith from a first orientation (e.g., stacked position 44) to a second orientation (e.g., side-by-side position 46). More particularly, for example, the guiding track 42 may comprise an element 60 located on one surface of the groove 48, such that when an assay bar is moved from one side 62 of the groove 48 to the other side 64, a notch in the protruding element 50 that is affixed to the assay bar will temporarily engage the element 60 and, by virtue of a force still being applied to move the assay bar from one side 62 of the groove 48 to the other side 64, the assay bar will be forced to rotate approximately 90-degrees. This will serve to convert an assay bar from a first orientation (e.g., stacked position 44) to a second orientation (e.g., side-by-side position 46).

The element 60 located on the surface of each groove 48 may comprise, for example, a dent that is configured to engage and be received by the notch located within each protruding element of the assay bar. As such, the element 60 and the notch in the protruding element 50 may function as a sort of gear (or set of gears), in re-orienting a series of assay bars from a first orientation to a second orientation, as they move past the element 60. According to such embodiments, the protruding element 50 is preferably configured to exhibit a cylindrical shape. This way, the protruding element 50 (with the connected assay bar) is allowed to rotate within the groove 48 about its longitudinal axis. That is, when the notch of the protruding element 50 engages the element 60 on the surface of the groove 48, and when the assay bar continues to travel from one side 62 of the groove 48 to the other side 64, the assay bar will be forced to rotate by approximately 90-degrees.

Frame-Shaped Guiding Tracks

Figure 7:
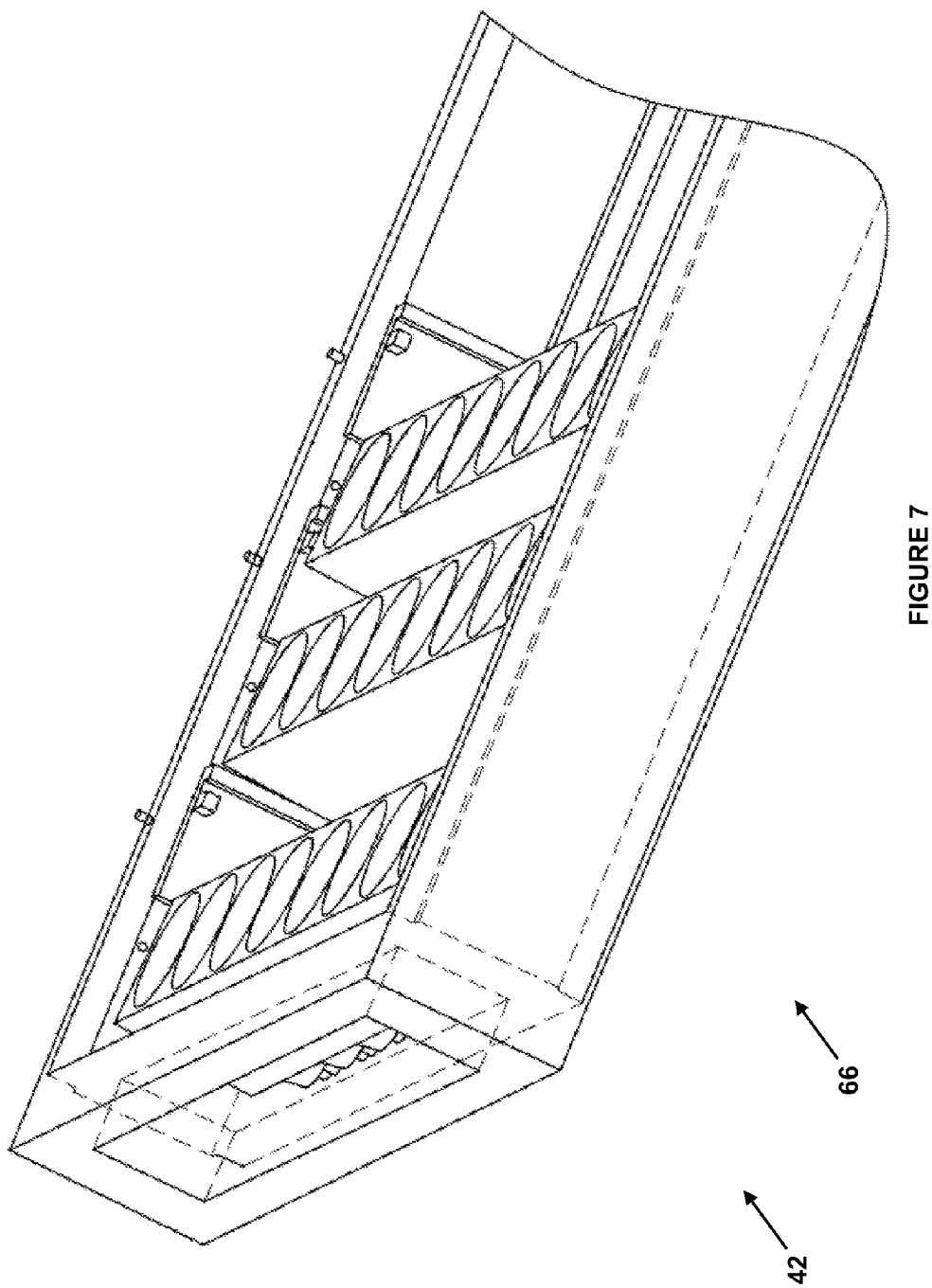
FIG. 7 is a perspective view of another guiding track of the present invention, which includes a set of telescoping rails.
Figure 8:
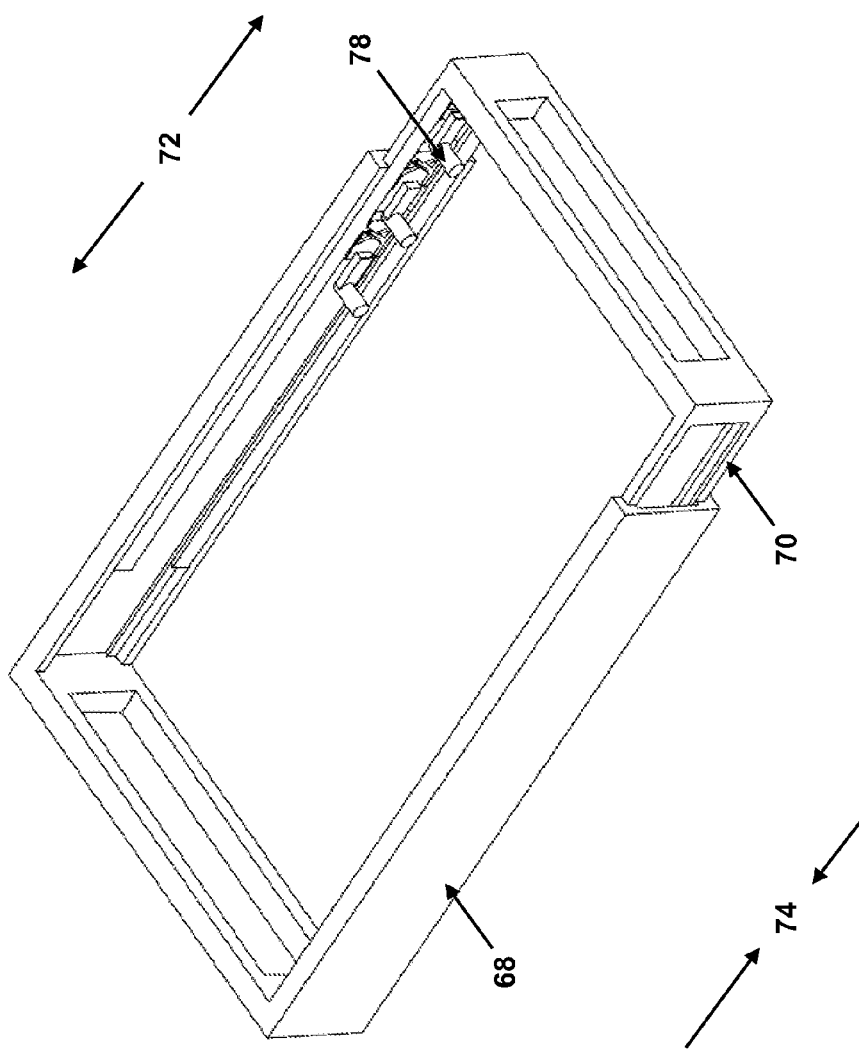
FIG. 8 is a perspective view of the guiding track of FIG. 7, which shows the interior portion telescopically pulled away from the exterior portion.

Referring now to FIGS. 7-15, according to yet further embodiments of the invention, the guiding tracks 42 may exhibit a frame-like configuration 66. More particularly, according to such embodiments, the two rails of the guiding track will include two telescoping parts. As shown in FIG. 8, the two rails will include an exterior portion 68 and an interior portion 70, which (along with two other sides) form a frame-like configuration. The telescoping parts, namely, the exterior portion 68 and interior portion 70, are configured to be reversibly and slidably (i) extended by pulling such parts away 72 from each other and (ii) contracted by pushing such parts closer 74 to each other.

According to these embodiments, both rails of the guiding track will include a plurality of movable sliders, which are configured to move linearly along the rails when the telescoping parts are moved relative to each other (i.e., pulled apart or pushed together). The sliders are connected to, or integrally formed with, certain pads 76 (which face the interior of the guiding track), each of which are configured to receive and be connected to an end of an assay bar. A pad 76 located on a first slider (which moves along the first rail) will be located directly across from a pad 76 located on a second slider (which moves along the second rail). As illustrated in FIG. 7, this allows a plurality of assay bars to be affixed to such pads 76, and held by the guiding track. The invention provides that when the telescopic parts of the rails are moved relatively to each other, the relative motion will be transmitted to at least one slider that is affixed to each rail, e.g., via a pin or a pad (not shown).

Figure 9:
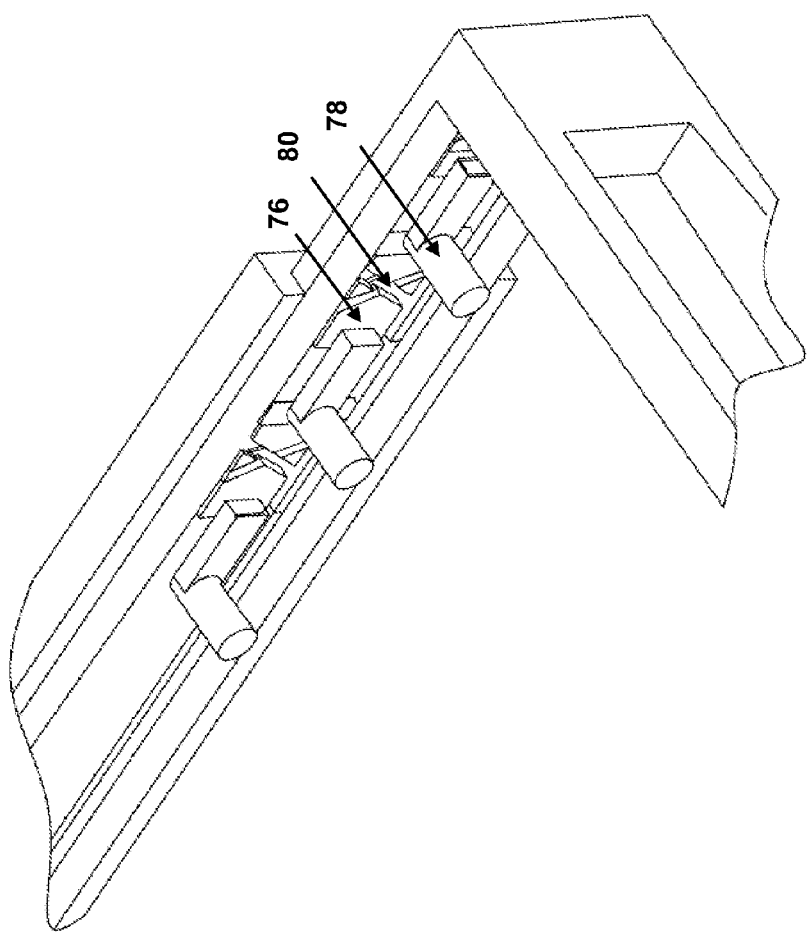
FIG. 9 is an illustration of the pins and grooves that comprise the assay bar pads described herein, which collectively operate to rotate the assay bars attached thereto, when the sets of telescopic rails are extended or contracted.
Figure 10:
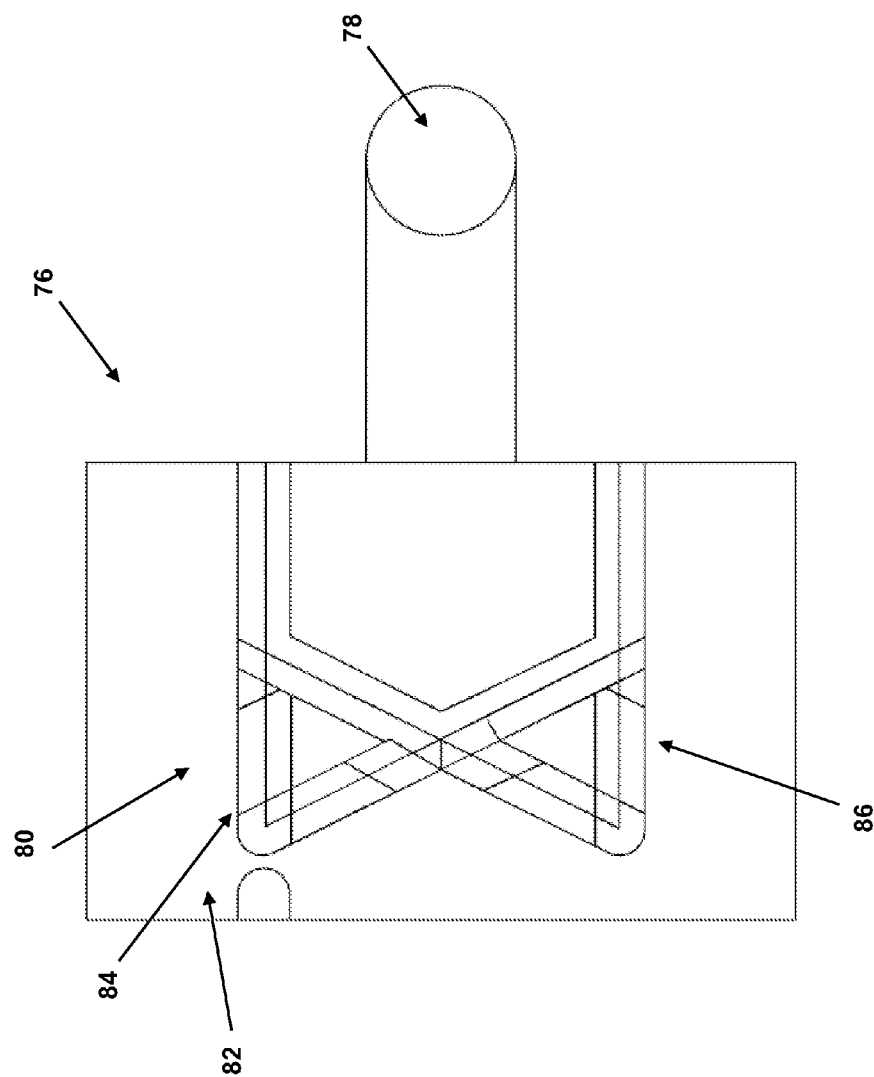
FIG. 10 is a side view of the pins and grooves that comprise the assay bar pads described herein.
Figure 12:
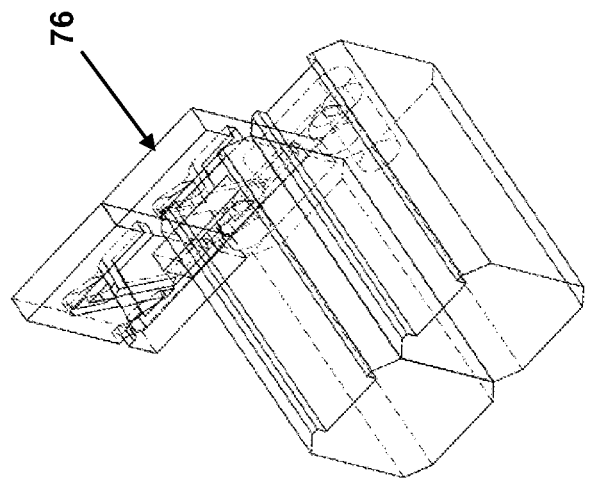
FIG. 12 is another perspective transparent view of the ends of the two assay bars connected to the assay bar pads that are shown in FIG. 11.
Figure 11:
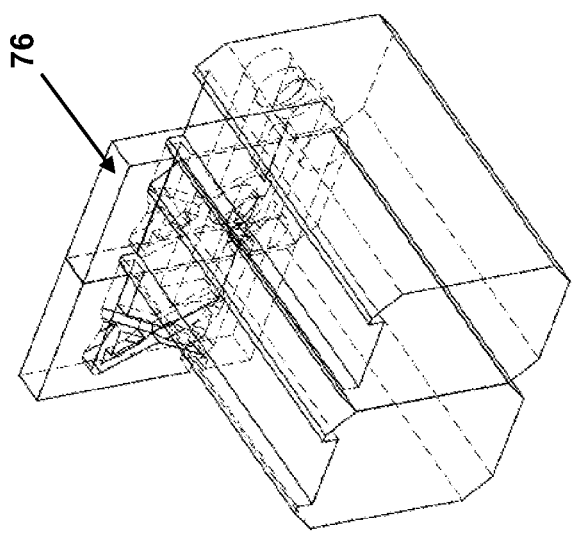
FIG. 11 is a perspective transparent view of the ends of two assay bars connected to the assay bar pads described herein.
Figure 14:
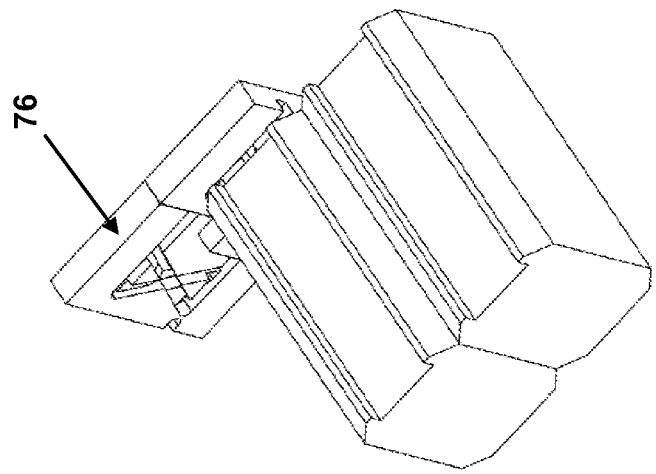
FIG. 14 is another perspective non-transparent view of the ends of the two assay bars connected to the assay bar pads that are shown in FIG. 13.
Figure 13:
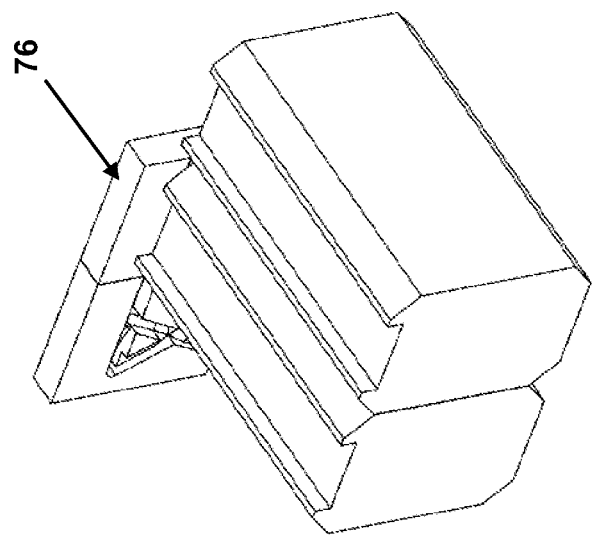
FIG. 13 is perspective non-transparent view of the ends of two assay bars connected to the assay bar pads described herein.
Figure 15A:
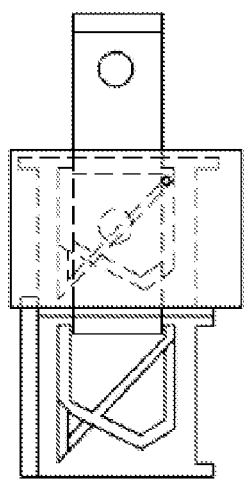
FIG. 15A-15G are side, partially transparent, views of an assay bar being rotated about its longitudinal axis, while being connected to an assay bar pad.
Figure 15B:
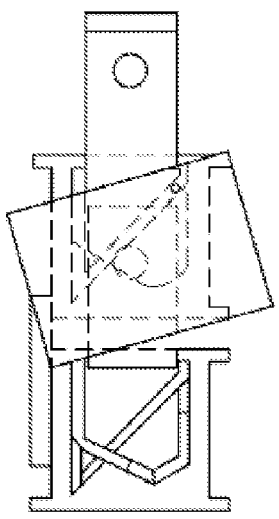
Figure 15C:
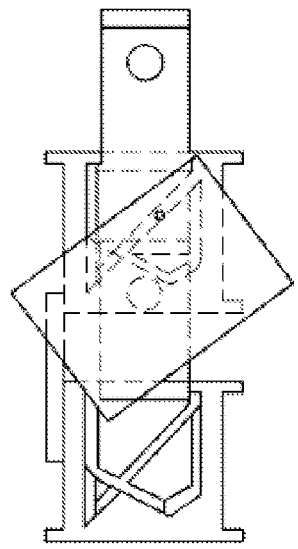
Figure 15D:
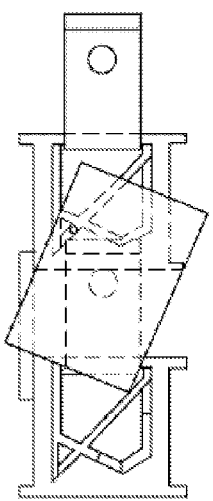
Figure 15E:
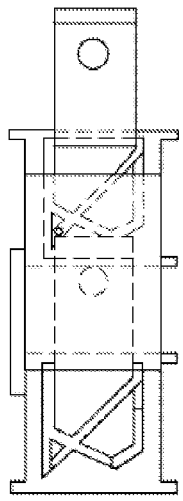
Figure 15F:
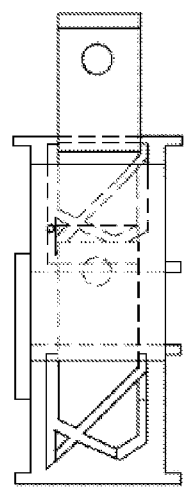
Figure 15G:
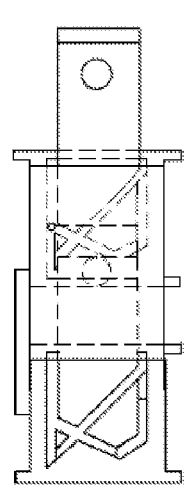

As illustrated in FIGS. 8-10, each pad 76 includes a pin 78 and set of grooves 80, which (together with the movable sliders) allow a plurality of assay bars connected to the guiding track (pads 76) to rotate around a longitudinal axis of such assay bars by 90-degrees in a first direction, when the telescoping components of such rails are pulled away from each other for a first time. Similarly, the pin 78 and grooves 80 allow the assay bars to rotate by 90-degrees around such longitudinal axis in an opposite (second) direction when the telescoping components of such rails are pulled away from each other for a second time. This functionality allows a user of the guiding track to easily and quickly convert the orientation of a set of assay bars from a stacked orientation to a side-by-side orientation (or vice versa). After the assay bars have been rotated, a user may contract the rails (push them together), in order to push the assay bars together.

More particularly, the invention provides that as the telescoping components of the guiding track rails move relative to each other (extended or contracted), the rails pull or push the sliders, which causes the sliders to move linearly along the rails (in the direction of the telescopic movement). The movement of the sliders, in turn, causes the assay bars (which are connected to the pads 76) to move as well. The pin 78 (which is connected to or integrally formed with the pad 76) is configured to be disposed through a corresponding aperture located in the end of an assay bar. The pad 76 comprises a flat body 82, with the set of grooves 80 located thereon (which face the interior of the guiding track), which are configured to receive one or more pins located at the end of the assay bar that is connected to such pad 76. The grooves 80 may comprise two horizontal and parallel grooves 84/86. The top horizontal groove 84 is preferably configured to terminate and turn downwards and become integrally formed with the bottom horizontal groove 86. Similarly, the bottom horizontal groove 86 is preferably configured to terminate and turn upwards and become integrally formed with the top horizontal groove 84. This configuration forms an X-like cross-dimensional shape, with the grooves 80 intersecting near a location between the horizontal and parallel grooves 84/86.

The invention provides that the pin 78 extends from pad 76 and transmits the linear motion of the sliders when the telescopic rails are pushed or pulled, while allowing a connected assay bar to rotate around its longitudinal axis. The grooves 80, in combination with a set of corresponding pins located on the ends of the assay bars, are configured to control the rotation of the assay bars around their longitudinal axis, as the telescopic rails are moved relative to each other. More particularly, the grooves 80, in combination with a set of corresponding pins located on the ends of the assay bars, are configured to control the rotation of the assay bars in such a manner that a user may selectively orient a plurality of assay bars that are connected to such pads 76 from a stacked orientation to a side-by-side orientation (or vice versa), by moving the telescopic rails relative to each other.

The invention provides that a pin 78 that extends from a first pad 76 is configured to be inserted into a corresponding aperture that is located at the end of an assay bar that connected to an adjacent (second) pad 76, whereas the grooves 80 of the first pad 76 controls the rotation of the assay bar that is connected to such first pad 76 (through a set of pins located at the end of such assay bar). Still further, the invention provides that as a first assay bar completes a 90-degree rotation (due to the extension or contraction of the telescoping parts), the guiding track will start rotating the next adjacent assay bar. FIGS. 15A-15G illustrate an assay bar rotating by 90-degrees about its longitudinal axis, as described herein.

The invention provides that when the telescopic rails are pulled apart from each other for a first time, a gap is first formed between neighboring assay bars. This gap allows the assay bars to rotate around their longitudinal axis. As described above, when the telescopic rails are pulled apart from each other for a first time, the assay bars are rotated by approximately 90 degrees in a first direction. The invention provides that when the telescopic rails are pushed back together, neighboring assay bars are forced back into contact with each other. When the telescopic rails are pulled apart from each other for a second time, a gap is again formed between neighboring assay bars, which allows the assay bars to rotate (by approximately 90-degrees) around their longitudinal axis in a second (opposite) direction. The telescopic rails may then be pushed back together, to force the neighboring assay bars back together—i.e., to eliminate the above-referenced gap and to allow the sides of the assay bars to make contact with each other.

More particularly, for example, the motion of the telescopic rails will be transmitted to a first slider (which is connected to or integrally formed with a first pad 76) by way of a set of pins or tabs. This first slider (and pad 76) will move linearly along the rail, thereby pulling the assay bar that is mounted on (or connected to) its pin 78, as the telescoping parts are pulled apart. Once this first assay bar has rotated by 90-degrees, a second adjacent slider will be pulled vis-à-vis a set of pins located at the end of the first assay bar being engaged within the grooves 80 of the second slider. The second slider will then move linearly with the second assay bar. Once the second assay bar has rotated by 90-degrees, a third slider will be pulled in the direction of the telescopic extension, and the above process will be repeated (until the telescopic movement has terminated and, preferably, all assay bars on the guiding track have been rotated). When the telescopic movement is reversed (e.g., when the rails are contracted instead of extended), the assay bars are forced back together (with the sides thereof directly adjacent to each other).

The guiding tracks described herein provide many benefits including, for example, the guiding tracks (1) provide for a smooth transition in re-orienting a series of assay bars from a stacked position 44 to a side-by-side position 46 (and vice versa) and (2) help to manage the order of the assay bars (so that a user is able to monitor which assay bars are being used to carryout a particular type of assay).

According to the foregoing embodiments, if the assay bars exhibit a number of wells 14 that are the same as those found in a row or column of a standard assay plate (e.g., a 96-well or 384-well assay plate), a series of the assay bars may be located adjacent to each other, in the side-by-side 46 configuration, to achieve the configuration and dimensions of a standard assay plate. For example, some assay plates comprise a total of 96 wells, configured with 12 columns and 8 rows of wells. If a series of assay bars comprise 8 wells 14, a series of 12 of such assay bars may be located adjacent to each other, in the side-by-side 46 configuration, such that the assay bars would collectively exhibit approximately the same dimensions (and number of wells 14) as a standard 96-well assay plate. In another example, if a series of assay bars comprise 12 wells 14, a series of 8 of such assay bars may be located adjacent to each other, in the side-by-side 46 configuration, such that the assay bars would collectively exhibit approximately the same dimensions (and number of wells 14) as a standard 96-well assay plate.

The invention provides that the assay bars may comprise a mechanical means (connection elements) on the exterior, side portions of the assay bars, which allow the assay bars to be reversibly and mechanically connected to each other when oriented in the side-by-side 46 configuration. Such mechanical means (connection elements) may include, e.g., snaps, tongue-and-groove elements, and others. For example, a first (left) side of an assay bar may comprise a male element, which may be received and mechanically connected to a female element located on a second (right) side of an adjacent assay bar.

According to such embodiments, a series of assay bars may be reversibly connected to each other, to exhibit the same dimensions (and number of wells 14) as a standard 96-well assay plate (or a 384-well assay plate). Such embodiments would allow a series of assay bars to, for example, be loaded into laboratory instrumentation that is configured to receive and handle a standard 96-well assay plate (or a 384-well assay plate), such as spectrophotometers, fluorometers, and other instruments that may be used to carryout the detection steps of a multiplex assay. According to certain embodiments, the guiding track may be configured to assist in locking the series of assay bars into a single unit, such that the assay bars (and the guiding track) may collectively be positioned into a detection instrument as described above.

According to still further embodiments of the present invention, the assay bars may comprise a handle, which may be gripped by a user to convert a series of assay bars from a stacked position 44 to a side-by-side position 46 (and vice versa). Such handles will preferably avoid direct contact between a user and the assay bars—and, for example, prevent the assay bars from becoming twisted and stuck in the grooves of a guiding track during a conversion from one orientation to another. In certain embodiments, the handle will allow a user to grip each assay bar, from a set of assay bars, and re-orient the assay bars from one orientation to another i.e., from a stacked position 44 to a side-by-side position 46 (and vice versa). In another embodiment, the handle may be used to unsnap or disconnect a particular assay bar from a set of connected assay bars, such that the gripped assay bar can be moved away from the other assay bars. In yet a further embodiment, the handle comprises a double beam mechanism, which allows a set of connected assay bars to be moved from one orientation to another. The invention further provides that, in certain embodiments, the handle may comprise two arms (at each end of an assay bar), which allow a user to grip both ends of an assay bar.

In yet another embodiment, the handle may be configured as the protruding elements 50/52, which may also be disposed into and through the grooves 48 of the guiding track 42. This way, the protruding elements 50/52 may serve two functions, namely, (1) to provide the element upon which an assay bar will travel along the grooves 48 of the guiding track 42 and (2) to serve as the handle described above. According to such embodiments, the handles (protruding elements 50/52) will preferably extend through the grooves 48 a sufficient distance to be accessible and capable of being gripped by a user of the assay system.

The invention provides that the dispenser bars 24, guiding tracks 42, and the assay bars described herein may be fabricated at low cost using plastic injection molding. For example, the dispenser bars 24, guiding tracks 42, and the assay bars may be comprised of polystyrene, polypropylene, polycarbonate, or other suitable materials. Still further, the invention provides that the dispenser bars 24, guiding tracks 42, and the assay bars may consist of multiple materials. For example, a majority of a bar may be manufactured from one of the plastics listed above, whereas the secondary containers 20 (or just the internal surface areas thereof) may be comprised of metals, glass, or other materials, e.g., by inserting a separate sleeve or tubing into such secondary containers 20. The molds that are necessary to fabricate the dispenser bars 24, guiding tracks 42, and the assay bars could be made by high-resolution machining, laser machining or micro-fabrication techniques to achieve the required precision. Still further, the invention provides that the guiding tracks 42 may, alternatively, be constructed from any of various metals and alloys.

Multiplex Binding Assays

The invention provides that the beginning of a multiplex binding assay may be carried out and set up using the assemblies described herein, by stacking a series of assay bars on each other, within a guiding track 42 described herein. Next, a dispenser bar 24 is placed on the top side 10 of the topmost assay bar (of the set of stacked assay bars). As described herein, the dispenser bar 24 will comprise one or more reservoirs 34, which are in fluid communication with the top end 26 of the secondary containers 20 of the assay bar located at the top of a stack of assay bars (and, indirectly, the secondary containers 20 of the assay bars located thereunder). This way, a desired reagent or other liquid may be loaded (filled) into a certain secondary container 20, or group of secondary containers 20, by dispensing an appropriate volume of such reagent or other liquid into the reservoir(s) 34 above the target secondary container(s) 20.

As mentioned above, the invention contemplates that different types of reagents or other liquids may be loaded into separate reservoirs 34 of the dispenser bar 24 and, therefore, into separate secondary containers 20 of an assay bar. Of course, the type of reagent(s) added to the secondary containers 20 (and well 14) of an assay bar will depend on the type of assay being performed. The invention does contemplate that, in addition to traditional reagents, such reagents may include micro-beads (including, without limitation, magnetic micro-beads).

Next, a reagent containing the desired receptors or antibodies (i.e., capture agents) are dispensed into the individual secondary containers 20 vis-à-vis the reservoirs 34 of the dispenser bar 24. Such receptors (capture agents) are then allowed to become bound to or immobilized on the interior surface of the secondary containers 20, or otherwise immobilized within the secondary containers 20 via magnetic or other forces, e.g., immobilizing the receptors (capture agents) that are bound to magnetic beads within the secondary containers 20 by placing (and optionally affixing) a magnetic element on the assay bar in sufficient proximity of the secondary containers 20 to retain such beads therein.

Next, such reagents are decanted out of the assay bar, while the immobilized receptors (capture agents) remain bound to the interior sides of the secondary containers 20 or otherwise retained therein via other forces. If multiple assay bars are employed, at this time, the various assay bars may be, optionally, converted to a side-by-side orientation 46, by moving the series of assay bars along the grooves 48 of the guiding track 42 described herein. The wells 14 and secondary containers 20 may be subject to a buffer rinsing step. The test samples may then be added to the secondary containers 20, e.g., by dispensing the samples into the wells 14, whereupon the test samples will enter the secondary containers 20 via capillary action and be allowed to interact with the immobilized receptors (capture agents) therein. The samples are then allowed to incubate for an appropriate period of time (and, if the above-referenced magnetic element is used, such element is removed from the assay bar during this incubation period).

According to such example, after the test samples are decanted from the assay bar, the secondary containers 20 may be rinsed with an appropriate buffer. Here again, if magnetic beads have been added to the secondary containers 20, the magnetic element should be returned and affixed to the assay bar during this rinsing step, in order to retain the beads inside the secondary containers 20. Following this rinsing step, if multiple assay bars are employed, the assay bars may be converted back to the stacked orientation 44 as described above.

A clean dispenser bar 24 is then placed on the top side 10 of the assay bar (or on the top side 10 of the assay bar located on a stack of assay bars). A specific secondary binding agent or antibody (i.e., the detection agent) may then be added to the secondary containers 20 of the assay bar(s) and allowed to incubate, in order to detect (and potentially quantify) agents, e.g., proteins, that were present in the sample and which bound to the immobilized receptors (capture agents). If magnetic beads are used, the magnetic element referenced above is removed from the assay bar(s) during this incubation period. The detection agent may be tethered to a molecule or agent, e.g., a fluorescent tag, which may be detected using standard instrumentation.

Following the appropriate incubation period for the detection agent, the assay bars may be separated and individually analyzed using an appropriate device to quantitate the amount of detection agent that has bound to immobilized sample agent that bound to the immobilized receptors (capture agents). Alternatively, and more preferably, the set of assay bars are converted to a side-by-side orientation 46, by moving the series of assay bars along the grooves 48 of the guiding track 42 described herein. According to such embodiments, the series of assay bars, in the side-by-side orientation 46, may then be analyzed together using an appropriate detection instrument (similar to how a standard microplate is analyzed in such instrumentation). The specific detection instrument that is used will depend on the nature of the detection agent, e.g., a fluorometer will be used to detect and quantify detection agents with fluorescent tags.

In addition to the assay bar assemblies described herein, methods of using the assay bars assemblies (and guiding track 42) for carrying out multiplex binding assays are encompassed by the present invention. The multiplex assay assemblies (and methods of use thereof) allow for the multiplexing of small volume samples—and for the separate dispensing of the reagents required by each of the multiplex assays. This way, each assay can be optimized individually, which leads to better assay quality (both in terms of reproducibility and sensitivity), and renders the modification of an assay panel possible without requiring the re-optimization of the entire panel.

Although certain example methods, apparatus, and/or articles of manufacture have been described herein, the scope of coverage of this disclosure is not limited thereto. On the contrary, this disclosure covers all methods, apparatus, and/or articles of manufacture fairly falling within the scope of the appended claims—either literally or under the doctrine of equivalents.

What is claimed is:

1. A multiplex binding assay assembly, which comprises:
   (a) at least one assay bar that comprises a top side, a bottom side, and at least one well accessible from the top side of the assay bar, wherein each well comprises a side surface, a bottom surface, an open top end, and at least one secondary container, wherein each secondary container comprises a capillary tube that (i) begins at a location within an interior volume of the well and (ii) ends at a location beneath the bottom side of the assay bar; and
   (b) a guiding track that comprises a set of two rails running parallel to each other, with a first rail being configured to receive a first end of the assay bar, and a second rail being configured to receive a second end of the assay bar, such that the assay bar is held perpendicularly to each rail, wherein the guiding track is further configured to allow the assay bar to move linearly along the set of two rails and to rotate around a longitudinal axis of the assay bar.

2. The multiplex binding assay assembly of claim 1, wherein each of the two rails comprises a groove, wherein the grooves run parallel to each other and each groove is configured to receive a protruding element of the assay bar, with the groove of the first rail configured to receive a protruding element of the first end of the assay bar, and the groove of the second rail configured to receive a protruding element of the second end of the assay bar, wherein the grooves are configured to allow the assay bar to glide linearly along the grooves from one side to a second side thereof.

3. The multiplex binding assay assembly of claim 2, wherein each of the two rails comprises two sections, which comprise a first vertical section running approximately perpendicular to a second horizontal section.

4. The multiplex binding assay assembly of claim 3, wherein the first vertical section of the rails is configured to hold a plurality of assay bars in a stacked orientation.

5. The multiplex binding assay assembly of claim 4, wherein the second horizontal section of the rails is configured to hold a plurality of assay bars in a side-by-side orientation.

6. The multiplex binding assay assembly of claim 5, wherein the plurality of assay bars are configured to glide along the first and second grooves from the first vertical section to the second horizontal section, in order to alter an orientation of the plurality of assay bars from the stacked orientation to the side-by-side orientation.

7. The multiplex binding assay assembly of claim 2, wherein the guiding track exists within a single plane, and comprises a means for rotating a plurality of assay bars connected to such guiding track by approximately 90-degrees.

8. The multiplex binding assay assembly of claim 7, wherein the means for rotating a plurality of assay bars comprises an element located on a surface of each groove, wherein upon a notch located within each protruding element of the assay bar engaging the element, the assay bar is forced to rotate approximately 90-degrees.

9. The multiplex binding assay assembly of claim 7, wherein the element located on the surface of each groove comprises a dent, which is configured to engage and be received by the notch located within each protruding element of the assay bar.

10. The multiplex binding assay assembly of claim 1, wherein each of the two rails of the guiding track comprises two telescoping parts, which are configured to be reversibly (i) extended by pulling such parts away from each other and (ii) contracted by pushing such parts closer to each other.

11. The multiplex binding assay assembly of claim 10, wherein:
(a) a set of sliders, each of which comprises a pad and a set of pins and grooves, located on the rails allows a plurality of assay bars connected to said pads to rotate around a longitudinal axis of such assay bars by 90-degrees in a first direction, when the telescoping components of such rails are pulled away from each other a first time; and
(b) the set of pins, or another set of pins and grooves, allow the assay bars to rotate by 90-degrees around said longitudinal axis in an opposite direction when the telescoping components of such rails are pulled away from each other a second time.

12. The multiplex binding assay assembly of claim 1, which further comprises a dispenser bar that is adapted to be positioned adjacent to the top side of the assay bar, which comprises one or more reservoirs that are configured to provide one or more reagents to the at least one secondary container located in each well of the assay bar.

13. The multiplex binding assay assembly of claim 1, which comprises a plurality of assay bars, which are identically configured and adapted to be stacked upon each other, wherein each well of each assay bar comprises multiple secondary containers that are arranged in an identical manner among each well of each of the assay bars.

14. The multiplex binding assay assembly of claim 13, wherein a plurality of secondary containers located in a first assay bar are in fluid communication with a plurality of secondary containers located in a second assay bar that is positioned and stacked directly beneath the first assay bar.

15. The multiplex binding assay assembly of claim 14, wherein each reservoir of the dispenser bar is in fluid communication with the at least one secondary container located in the assay bar, when the dispenser bar is positioned adjacent to the top side of the assay bar.

16. The multiplex binding assay assembly of claim 15, wherein each reservoir is in fluid communication with at least one secondary container located in a first assay bar that is stacked upon a plurality of additional assay bars, when the dispenser bar is positioned adjacent to the top side of the first assay bar.

17. The multiplex binding assay assembly of claim 16, wherein each secondary container comprises a capillary tube that exhibits a length that is approximately equal to a distance between the top side and the bottom side of the assay bar.

18. The multiplex binding assay assembly of claim 17, wherein a top end of each secondary container is recessed relative to the top side of the assay bar.

19. The multiplex binding assay assembly of claim 18, wherein a bottom end of each secondary container extends below a plane that runs tangential with the bottom side of the assay bar.

20. The multiplex binding assay assembly of claim 19, wherein the bottom end of each secondary container extends below the plane that runs tangential with the bottom side of the assay bar by a distance of $\Delta_1$, wherein the distance of $\Delta_1$ equals the distance between the top end of each secondary container and the top side of the assay bar.

* * * * *